United States Patent [19]

Malek et al.

[11] 4,259,103

[45] Mar. 31, 1981

[54] METHOD OF REDUCING THE NUMBER OF MICROORGANISMS IN A MEDIA AND A METHOD OF PRESERVATION

[75] Inventors: James R. Malek; John L. Speier, both of Midland, Mich.

[73] Assignee: Dow Corning Corporation, Midland, Mich.

[21] Appl. No.: 38,997

[22] Filed: May 14, 1979

Related U.S. Application Data

[63] Continuation-in-part of Ser. No. 19,532, Mar. 12, 1979, abandoned.

[51] Int. Cl.³ .................. A01N 9/20; A01N 17/00; A61K 9/00
[52] U.S. Cl. ............................. 71/67; 424/16; 424/25; 424/287
[58] Field of Search .............. 424/16, 25, 26, 27, 424/28, 78, 31, 287; 71/67

[56] References Cited

U.S. PATENT DOCUMENTS

| | | | |
|---|---|---|---|
| 3,227,614 | 1/1966 | Scheuer | 424/25 |
| 3,624,224 | 11/1971 | Watchung | 424/25 |
| 3,794,736 | 2/1974 | Abbott et al. | 424/78 |

*Primary Examiner*—Delbert R. Phillips
*Assistant Examiner*—Blondel Hazel
*Attorney, Agent, or Firm*—Robert L. McKellar

[57] ABSTRACT

What is disclosed is a method of reducing microorganisms by contacting the microorganisms with the surface of a substrate which has been altered by contacting a substrate which develops a negative charge in water with a substance that ionizes in water to form cations and anions, which cations absorb to the substrate by a process of ion exchange in which protons are replaced by the cations of the ionizing substance. The altered surfaces can include hospital sheeting, clothing and a wide variety of surfaces which come into contact with microorganisms.

26 Claims, No Drawings

METHOD OF REDUCING THE NUMBER OF MICROORGANISMS IN A MEDIA AND A METHOD OF PRESERVATION

BACKGROUND OF THE INVENTION

This application is a continuation-in-part application of Ser. No. 19,532, filed Mar. 12, 1979 now abandoned.

Almost concurrently with the notion that microorganisms cause infection and disease came the discovery that the microorganisms could be controlled either by killing all of them or reducing their numbers significantly.

Many methods have been devised that would accomplish the end result including reducing all known infected things to ashes. As a practical matter, because all such infected things could not be summarily subjected to such treatment, other, more specific methods were devised to control the microorganisms. One such specific method was the treatment of milk and similar products, at elevated temperatures high enough to destroy objectional organisms but not high enough to alter the chemical characteristics of the milk. This method was developed by Louis Pasteur during the mid-nineteenth century. Sterilization where foodstuffs were not involved constituted the use of chemicals such as phenol. Phenol is effective but is a very harsh chemical in terms of its acidic properties. Similar microbial poisons have been commercially available for a number of years. Certain amines and their quaternary salts, boric and carboxylic acids and their salts and a host of other chemicals have been used. These materials were used neat or in aqueous solutions and then placed on the substrate to be sterilized.

The utility and commercial potential of bacteriostatic properties of certain cationic nitrogen compounds is well known and seems first to have been recognized about 1935 in U.S. Pat. No. 2,108,765 and, G. Domagk, "A New Class Of Disinfectant Materials", Deut. Med. Wochn., 61, 829 (1935). Domagk recognized that if at least one group in an amine was sufficiently large and properly hydrophobic to give the molecule surfactant properties in water, such a molecule then had bacteriostatic or bacteriocidal properties. Following these publications, scores of cationic surfactants were found to have antimicrobial properties, and the teaching of Domagk was proved to be correct.

It is observed that surfactant properties and antimicrobial activity are found in common among compounds with at least one positively charged nitrogen atom and at least one hydrophobic group. The hydrophobic group should be equivalent to an aliphatic group of at least $C_8H_{17}$- and not larger than $C_{22}H_{45}$-.

An excellent review of the antimicrobial behavior of cationic substances in solution is to be found in "Cationic Surfactants", Marcel Dekker, Inc., New York, 1970, especially Chapter 14, Carl A. Lawrence-"Germicidal Properties of Cationic Surfactants"; and Chapter 11, Martin E. Ginn, "Adsorption of Cationic Surfactants on Miscellaneous Solid Substrates".

Researchers have investigated ways in which substances which were proven to be useful antimicrobials in solution could be made more persistent on substrates. One such way was to attach an antimicrobial agent to a substrate by some means.

In one method, an antimicrobial agent was mixed with a curable coating. This method was quite satisfactory for prolonging the residence of the antimicrobial agent but problems were still encountered as the antimicrobial agent leached from the coating and was washed away.

A better method evolved around 1965 when researchers discovered that antimicrobial organofunctionalsilanes could be chemically bound to certain substrates by what were believed to be Si-O linkages. The method was described as orienting the organofunctional silane in such a way that hydrolyzable groups on the silicon atom were hydrolyzed to silanols and the silanols formed chemical bonds with the substrate and the antimicrobial end of the molecule, for example a quaternary nitrogen, was oriented away from the substrate; P. A. Walters, E. A. Abbott and A. J. Isquith, Applied Microbiology, Feb. 1973, pages 253-256. Theories abiding at the time alleged that any molecule having a reactive silyl group to bind to a surface and which also displayed antimicrobial activity in solution would function this way. In other words, if the molecule had activity in solution, this activity could be fixed to a surface by means of the silanol groups. The fixation would be so strong that little or no material would be removed from the surface by water. Thus, such a surface would affect microorganisms in water without loss of the active structure from the surface.

The theory could not be substantiated because no method existed by which the theory could be tested. The methods available were designed to measure the activity of an agent in solution, and this fact is important because the present invention deviates significantly from that theory and greatly increases the number and variety of substances that can be useful to render surfaces antimicrobial.

A clear statement of the theory that a totally bound substance could not affect microorganisms can be found in L. A. Vol'f, "Imparting Antimicrobial Properties to Fibers", Tekstilnaya Promnyshlenmost No. 8, 9 (1965), U.S.S.R. (Translation by Techtron Corp.), who stated, "Imparting antimicrobial activity to fibers can be carried out in two ways: (1) by sorption of a chemotherapeutic preparation or antiseptic agent (with subsequent desorption) and (2) by chemical linking of the fiber with compounds which impart to the fibers an anti-bacterial effect (with their subsequent cleavage)." Speaking of method (2) Vol'f goes on to state, "The problem of the fixation of antimicrobial substances on the fiber by means of a chemical bond contains at first sight, two contradictory postulates. Actually on the one hand it is dictated by the effort to prevent the removal of groupings which are responsible for the antimicrobial effect from the fiber during use and on the other hand it is necessary to assume the transportation (diffusion) of these groups within the microbial cells for otherwise, the main goal of destroying the pathogenic microflora at a distance will not be achieved." He also adds, ". . . the necessary condition for the manifestation of antibacterial action is the presence of moisture. It is precisely this which accomplishes the transport of active ingredients to the microorganisms."

In 1967, Canadian Pat. No. 774,529 was issued and was completely contrary to Vol'f's opinion. This patent stated that antimicrobial activity could in fact be put on a substrate by binding an antimicrobial organosilicon compound to a substrate but this patent showed no example of how this should be done, nor an example that this had been done. The first example in which this was thought to be demonstrated was taught clearly by Isquith et al. later in a publication; A. J. Isquith, E. A. Abbott and P. A. Walters, Applied Microbiology, December, 1972, Pages 859–863. In this publication they taught that only cationic antimicrobial agents which were substituted by a (CH$_3$O)$_3$Si- group could display antibacterial activity when deposited on a surface.

P. A. Walters, E. A. Abbott and A. J. Isquith, Applied Microbiology, 25, No. 2, p. 253–256, Feb. 1973 amplified this teaching. They taught that 3-(trimethoxysilyl)propyldimethylalkylammonium chlorides, with alkyl chain lengths from 6 to 22 carbons in solution were capable of killing algae. They state, "these compounds retained biological activity when durably attached to a surface". They further teach that this was a "unique property" of these compounds and that such closely similar compounds as the commercial Benzalkonium chlorides (Winthrop Laboratories, Division of Sterling Drug Inc., New York, NY) did not display this property.

The teaching was further amplified by E. A. Abbott and A. J. Isquith, U.S. Pat. No. 3,794,736, Feb. 26, 1974. In this patent they teach that a variety of siloxane-substituted amines and amine salts which display antibacterial and antifungal properties in solution, continue to display these properties when the substances were deposited on surfaces. They claimed a method of inhibiting growth of bacteria and fungi by contacting said organisms with a surface that had been coated with a variety of siloxane-substituted organic amines or their salts.

One substance favored by these investigators has been adopted for commercial use to prepare antimicrobial surfaces. This substance is essentially a methanol solution of (CH$_3$O)$_3$Si(CH$_2$)$_3$N(CH$_3$)$_3$C$_{18}$H$_{37}$+Cl−.

The use of a filler, e.g. silica or titanium dioxide, which had been treated with an organosilicon-substituted quaternary ammonium salt, to inhibit the growth of micro-organisms in or on the surface of a polymeric organic matrix into which the filler had been incorporated was taught in Canadian Pat. No. 1,010,782, issued May 24, 1977, to Roth.

This is a new way to use a surface treated as taught by Isquith, et al. and Roth was surprised to discover that a filler treated with 10% by weight of (CH$_3$O)$_3$-Si(CH$_2$)$_3$NC$_{18}$H$_{37}$(CH$_3$)$_3$+Cl− was effective, unexpectedly contrary to the teaching of Isquith, et al. in that this substance is not antimicrobial in solution.

Thus, it can be observed that all prior art indicates that antimicrobial systems can be prepared by (1) treatment of surfaces with harsh chemicals; (2) chemical bonding of chemical agents to substrates.

The Invention

It has now been discovered that there is a significantly better way to reduce the number of viable microorganisms. By changing the surface characteristics of a substrate and then contacting microorganisms with the changed surface of the substrate, the microorganisms are killed.

Thus what is disclosed is a method of reducing the number of viable microorganisms in media by physically contacting the microorganisms with a surface which has been altered in a manner which comprises contacting a substrate, which develops a negative charge in water, with a substance that ionizes in water to form cations and anions, which substance consists of organic amines having the formula R$^1$R$^2$R$^3$N in which R$^1$, R$^2$ and R$^3$ are independently hydrogen, alkyl or aralkyl groups wherein there is a total of less than 30 carbon atoms in the molecule; an organic quaternary ammonium salt of the formula R$^4$R$^5$R$^6$R$^7$N+X− wherein R$^4$, R$^5$, R$^6$ and R$^7$ are independently alkyl or aralkyl groups wherein there is a total of less than 30 carbon atoms in the molecule and X− is a water soluble monovalent anion; a sulfonium salt of the formula R$^8$R$^9$R$^{10}$S+X− in which R$^8$, R$^9$, and R$^{10}$ are independently alkyl groups or aralkyl groups wherein there is a total of less than 30 carbon atoms in the molecule or a silylsubstituted alkyl radical of the formula

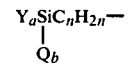

in which Y is a hydrolyzable group, Q is an alkyl radical of 1 or 2 carbon atoms of (CH$_3$)$_3$SiO, a has an average value of 0–3; b has an average value of 0–3, n is an integer of 1 or greater and X− is a water soluble monovalent anion; an isothiuronium salt of the formula RSC(NH$_2$)$_2$+X− in which R is independently alkyl or aralkyl groups wherein there is a total of less than 20 carbon atoms in the molecule or a silyl substituted alkyl radical of the formula

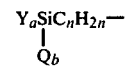

in which Y is a hydrolyzable group, Q is an alkyl radical of 1 or 2 carbon atoms or (CH$_3$)$_3$SiO, a has an average value of 0–3; b has an average value of 0–3, and n is an integer of 1 or greater and X− is a water soluble monovalent anion; a phosphonium salt of the formula R$^4$R$^5$R$^6$R$^7$P+X− in which R$^4$, R$^5$, R$^6$ and R$^7$ are independently alkyl groups or aralkyl groups wherein there is a total of less than 30 carbon atoms in the molecule or a silyl substituted alkyl radical of the formula

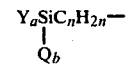

in which Y is a hydrolyzable group, Q is an alkyl radical of 1 or 2 carbon atoms or (CH$_3$)$_3$SiO, a has an average value of 0–3; b has an average value of 0–3, n is an integer of 1 or greater and X− is a water soluble monovalent anion; a sulfonium salt of the formula O[-Si(CH$_3$)$_2$C$_d$H$_{2d}$S+(R$^{11}$)$_2$X−]$_2$ in which R$^{11}$ is independently an alkyl group or aralkyl group wherein there is a total of less than 60 carbon atoms in the molecule, d is an integer of 1 or greater and X− is a water soluble monovalent anion; an isothiuronium salt of the formula O[Si(CH$_3$)$_2$C$_d$H$_{2d}$S+C(NH$_2$)$_2$X−]$_2$ in which d is an integer of 1 or greater and X− is a water soluble monovalent anion; a phosphonium salt of the formula O[-Si(CH$_3$)$_2$C$_d$H$_{2d}$P+(R$^{12}$)$_3$X−]$_2$ in which R$^{12}$ is independently an alkyl group or aralkyl group wherein there is a total of less than 60 carbon atoms in the molecule, d is an integer of 1 or greater and X− is a water soluble monovalent anion and, an organic amine of the formula

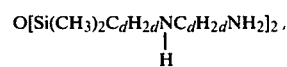

in which d is an integer of 1 or greater.

The value of n is normally 1–10 carbon atoms. For all practical purposes, d generally has a value of 1–10 carbon atoms.

As can be observed, the size of the alkyl or aralkyl groups is dependent on the type of substance that is being utilized. Thus, if the material is an organic amine of the formula $R^1R^2R^3N$, a quaternary ammonium salt of the formula $R^4R^5R^6R^7N^+X^-$, a sulfonium salt of the formula $R^8R^9R^{10}S^+X^-$ or a phosphonium salt of the formula $R^4R^5R^6R^7P^+X^-$, the total number of carbon atoms in the molecule can be as large as 30 while the isothiuronium salts of the formula $RSC(NH_2)_2^+X^-$ require a total of 20 carbon atoms or less. When the substance is a sulfonium salt of the formula $O[Si(CH_3)_2C_dH_{2d}S^+(R^{11})_2X^-]_2$ or a phosphonium salt of the formula $O[Si(CH_3)_2C_dH_{2d}P^+(R^{12})_3X^-]_2$, the total number of carbon atoms in the molecule can be as large as 60. It should be understood that as regards the latter sulfonium and phosphonium salts, this invention does not contemplate alkyl or aralkyl groups of 60 carbon atoms but instead contemplates a disiloxane which contains alkyl or aralkyl groups on each sulfur or phosphorus atom such that there are less than 30 carbon atoms per each sulfur or phosphorus per molecule. The size and type of the alkyl or aralkyl group is significant in that the larger groups contribute to the permanence of the surface alteration which in turn contributes to the permanence of the antimicrobial effect.

Bulky organic cations adsorb very strongly to substrates. If the organic groups have straight chain alkyl configurations then they tend to lay closely packed, side by side, extending essentially upward from the substrate surface. This closer proximity leads to bonding between the alkyl groups through Van der Waals' forces or some similar effect. This increased bonding mechanism tends to enhance the permanence of the cationic surface.

For purposes of this invention, generally one or two large alkyl or aralkyl groups on the molecule are used. For all practical purposes, molecules containing more than two large alkyl or aralkyl groups are hard to prepare and further they tend to be too bulky to give the optimum bonding between groups necessary for this invention. Preferred for this invention are those compounds that contain at least one alkyl or aralkyl group having greater than 10 carbon atoms.

$X^-$ for purposes of this invention is a water soluble monovalent anion. Examples of preferred anions are $Cl^-$, $Br^-$, $I^-$ and $CH_3COO^-$.

The advantages of the newly discovered method are that a very large variety of surfaces, which include all which develop a negative charge in contact with water, can be altered to have antimicrobial activity by treatment with a very large variety of substances which need have no biocidal activity in solution, but which need only to ionize in solution in water to form a cation other than a proton.

The most critical aspect of this invention is the fact that the interface between surfaces of the substrates of this invention and water must be altered. It should be understood that the substrate is not chemically altered. The interface between the surface of the substrate and water is altered in that adsorbed water on the surface is altered. Substrates that fall within the scope of this invention are any substrates which develop a negative charge on their surfaces in the presence of water. Such things as fibers, textiles, particulate materials such as sand, earth, concrete and masonry surfaces, wood, plastics and polymers all develop negative charges on their surfaces in the presence of water.

The adsorption of cations upon mineral surfaces from water has been studied extensively for many years and a carefully detailed theory of the physical chemistry of the process has been developed. The adsorption of cations upon organic surfaces has also been extensively studied, although the theory in this case is not as completely developed. The concept that an electrically charged layer develops at a solid-liquid boundary or interface has been accepted for at least as long as 160 years (F. Reuss, 1809, R. Porret, 1816). That a process of ion exchange occurs in this charged layer has been believed for at least 100 years (H. von Helmholtz, 1879). A mathematical semi-quantitative description of the process was well developed at least 50 years ago. (O. Stern, 1924). Any good textbook on the physical chemistry of surfaces describes these phenomena. See S. Glasstone, Text-Book of Physical Chemistry, D. Van Nostrand Company, Inc. New York, NY (1940) pp. 1194 et seq.

When surfaces are subjected to solutions of a cationic material as later defined in this specification, for example, a cationic surfactant, the surface is altered to the extent that hydrogen ions of adsorbed water are removed from the surface and moved to the bulk water and the cations move to the surface. It is theorized, but the inventors do not wish to be held to such a theory, that the cations replace hydrogen ions of water adsorbed on the surface of the substrate until the cations are packed very closely together. Further, if the cationic material also contains appropriate groups in the molecule (as explained later in this specification), the alteration is permanent and the substrate surface remains antimicrobial.

Water adsorbed on the substrate is highly ionized, thus $H^{30}$ $OH^-$. When such a surface is treated with a cationic material, the hydrogen ions of the adsorbed water preferentially move to the surrounding bulk water and the cation of the cationic material moves preferentially to the surface. Thus, it is theorized that there is an equilibrium at the surface i.e. $H^+$ $OH^-+H_2O \rightleftharpoons HO^- +H_3O^+$. When the cations from the cationic material approach the surface the equilibrium is upset and shifted to the right. There then exists on the surface of the substrate, a tightly held, adsorbed system consisting of the new cation and the adsorbed water hydroxyl. The major discovery of this invention is that surfaces so modified by cations are antimicrobial to any microorganism that physically contacts them.

The second critical aspect of this invention is the fact that the microorganisms must physically contact the altered surface. By way of example, if the substrate is glass beads which have been treated as discussed above and the media is aqueous, for example, milk, and the two are mixed together and stirred with a spatula for a few minutes, then this would be sufficient force to get the desired effect. Similarly, flowing a thin film of beer across an altered surface, such as polyethylene, would be enough force to get the desired effect. A third example would be stirring a solution containing the appropriate materials with a powered stirrer with enough speed to make a vortex in the solution. A fourth example would be blowing contaminated air through a filter, such as a furnace filter, which has been treated to make its surface antimicrobial, according to this invention. The amount of force required is a function of the particular system being used.

Once the surface of the substrate has been altered, microorganisms that contact the surface are destroyed. In certain examples there is no transfer of cationic material into the media and since the adsorbed surface is not susceptible to erosion or leaching, the substrate can be used over and over without destroying its effectiveness.

Contemplated within the scope of this invention is any substrate which develops a negative charge in water.

A surface suitably treated is essentially impervious to attack by microorganisms. A surface in a medium which supports the growth of microorganisms has no apparent effect upon organisms in the medium, but organisms that contact the surface are killed. If the medium is stirred to cause organisms to contact the surface, the organisms can all be killed. In the absence of stirring, no noticeable number of organisms are killed, but the surface is protected from attack by the organisms, thus, there is a preservative effect contemplated within the scope of this invention.

Substrates that develop negative charges in water at a pH below about 10 are suitable for the method of this invention. These include all known textile fibers, such as cotton, cellulose acetate, polyesters, nylon, wool, rayon, acrylon, etc.; all known organic surfaces, such as paints, polystyrene, silicone polymers, wood, rubber, etc.; almost all inorganic surfaces, such as silica, sand, earth, silicate minerals, alumina, glass, including concrete and masonry surfaces etc. which are not soluble in water.

Substances capable of making these substrates antimicrobial are those that ionize in water to form cations to exchange with protons in the layer of water adsorbed onto the substrate. These include such diverse materials as sodium chloride, ammonium chloride, every type of amine, primary, secondary or tertiary, as well as quaternary ammonium salts, diamines, isothiuronium salts, sulfonium salts, and phosphonium salts. No antimicrobial activity of the substances in solution is required nor is the activity in solution of any influence on the level of antimicrobial activity shown by surfaces of substrates treated with these substances.

Cations that contain bulky organic substituents are adsorbed to surfaces more strongly. They do not give rise to more active surfaces, but they do give rise to surfaces that are more resistant to loss of activity through loss of the cation from the surface.

Cations that contain silyl substituted organic substitutents have a unique advantage over other cations. Cations having substituents such as $(CH_3O)_3Si$- hydrolyze and polymerize and become essentially irreversibly bound.

The manner of putting these substances on the surface of a substrate is critical to a degree. It is possible to spray, dip, paint or roll on the cationic material or in the case of particulate solids dispersions may be used or in the case of fibers soaking techniques may be used. The length of time that contact between the cationic material and the substrate is necessary depends on the substrate and the type of cationic material being used. Fibers for example should not be treated for long periods of time unless the surface of the internal fibers is to be treated. Times of contact can range from a few seconds to a few hours and the time required is that time necessary to exchange the hydrogen ions of the adsorbed water on the surface for cations.

In actual practice, it is sometimes desirable to rinse the surface of the substrate after being treated.

The time required for rinsing the surface is not critical. Generally water is used for this purpose but water and organic solvents can be used. For example, a rinse with a mixture of alcohol and water and then a clear rinse with water is generally sufficient.

Some of the advantages of the method of this invention are: Subtances chosen for use in this invention may be inoccuous compounds that are not toxic, corrosive, or hazardous to any appreciable extent. They do not have to be biologically hazardous substances.

Exceedingly small quantities of the substances are capable of killing an apparently limitless number of organisms that contact a properly treated surface.

It can be noted, for example, that in Test No. 13 of Example 1, as low as 0.03 g. ion/100 $Å^2$ was sufficient to give 100% reduction of microorganisms in only 1 treatment.

No substance needs to enter media in which the microorganisms are found. Thus a medium need not be contaminated by an antimicrobial agent to obtain a very strong antimicrobial effect.

A properly treated surface is capable of killing most diverse spectra of microorganisms.

Now, so that those skilled in the art can better understand and appreciate this invention, the following examples are given. The examples following hereafter give those skilled in the art the guidance necessary to practice this invention.

EXAMPLE 1

Many substrates were coated with materials by a "Paint on Technique". By this method a known amount of a chemical in solution was used to wet a solid. The solvent was evaporated and the amount of chemical in solution was deposited on the surface of the solid.

Table I shows surprising results obtained when finely divided powders are mixed mechanically with cultures of microorganisms in what is called "The Powder Test".

In the Powder Test, a quantity between 0.1 and 0.5 g., depending upon the particle size and density of a finely divided solid, was weighed into a clean Pyrex test tube. A sample treated with a chemical by the Paint on Technique, and an equal sized sample of untreated sample were each mixed thoroughly (on a Vortex mixer) for 15 seconds and placed in an incubator for 30 minutes at 37° C.

Each sample was then agitated for 10 seconds with 10 ml. of sterile broth. A 0.1 ml. portion of the broth was agar plated and incubated 18 hours. After this time the number of viable organisms extracted from a treated sample was compared with the number extracted from an untreated sample. The percent reduction of viable cells was calculated from the difference between these values, i.e. (No. of cells from untreated sample-No. of cells from treated sample divided by No. of cells from untreated sample) × 100 = % Reduction.

If no living organisms were extracted, the sample was said to have achieved 100% kill.

This technique permits the evaluation of the antimicrobial activity of a large surface area in relatively small volumes.

The data in Table I was obtained by use of 0.1 ml. of 1:100 dilution of an 18 hour culture of Escherichia coli B.

In many cases the sample was washed and extracted with water before being subjected to the powder test. Typically, about 1 g. of sample was mixed thoroughly with about 10 ml. of distilled water and the mixture was filtered or centrifuged and sucked dry in a vacuum filter. Sometimes samples were washed in this way many times.

In Table I, the following compositions are shown wherein the following Test Nos. correspond to the Test Nos. in the Table:

| Test No. | Substance tested |
|---|---|
| 1 | $(CH_3)_4N^+Cl^-$ |
| 2 | " |
| 3 | " |
| 4 | " |
| 5 | " |
| 6 | " |
| 7 | " |
| 8 | " |
| 9 | $Na^+Cl^-$ |
| 10 | $NH_4^+Cl^-$ |
| 11 | $C_{18}H_{37}N(CH_3)_3{}^+I^-$ |
| 13 | " |
| 14 | " |
| 15 | $C_{18}H_{37}N(CH_3)_2$ |
| 16 | Zephiran[j] |
| 17 | $n\text{-}C_6H_{13}NC_5H_5{}^+Cl^-$ |
| 18 | " |
| 19 | $n\text{-}C_4H_9N(CH_3)_3{}^+Cl^-$ |
| 20 | $(n\text{-}C_4H_9)_2N(CH_3)_2{}^+Cl^-$ |
| 21 | $n\text{-}C_4H_9\text{-}C_8H_{17}N(CH_3)_2{}^+Cl^-$ |
| 22 | $(C_2H_5)_3N$ |
| 23 | " |
| 24 | $n\text{-}C_4H_9NH_2$ |
| 25 | " |
| 26 | $(C_2H_5)_2NH$ |
| 27 | " |
| 28 | $(CH_3O)_3Si(CH_2)_3N(CH_3)_3{}^+Cl^-$ |
| 29 | $(CH_3O)_3Si(CH_2)_3N(CH_3)_3{}^+Cl^-$ |
| 30 | " |
| 31 | $(CH_3O)_3Si(CH_2)_3N(CH_3)_3{}^+OH^-$ |
| 32 | $(CH_3O)_3Si(CH_2)_3N(C_2H_5)_3{}^+I^-$ |
| 33 | $(CH_3O)_3Si(CH_2)_3N(C_2H_5)_3{}^+Cl^-$ |
| 34 | $(CH_3O)_3Si(CH_2)_3N(C_2H_5)_2$ |
| 35 | $(CH_3O)_3Si(CH_2)_3NHCH_2CH_2NH_2$ |
| 36 | $\{(CH_3)_3SiO\}_3Si(CH_2)_3NHCH_2CH_2NH_2$ |
| 37 | " |
| 38 | $(CH_3O)_3Si(CH_2)_3NC_5H_5{}^+Cl^-$ |
| 39 | " |
| 40 | " |
| 41 | $(CH_3O)_3Si(CH_2)_3N(CH_3)_2C_8H_{17}{}^+Cl^-$ |
| 42 | $(CH_3O)_3Si(CH_2)_3N(CH_3)_2C_4H_9{}^+Cl^-$ |
| 43 | $(CH_3O)_3Si(CH_2)_3N(CH_3)_2C_{18}H_{37}{}^+Cl^-$ |
| 44 | " |
| 45 | " |
| 46 | " |
| 47 | $(CH_3O)_3Si(CH_2)_3P(n\text{-}C_4H_9)_3{}^+I^-$ |
| 48 | $(CH_3O)_3Si(CH_2)_3P(C_6H_5)_3{}^+I^-$ |
| 49 | $(CH_3O)_3Si(CH_2)_3SC(NH_2)_2{}^+Cl^-$ |
| 50 | $CH_3SC(NH_2)_2{}^+Cl^-$ |
| 51 | $(CH_3O)_3Si(CH_2)_2S(CH_3)C_{18}H_{37}{}^+I^-$ |
| 52 | " |
| 53 | $(CH_3O)_3Si(CH_2)_3S(CH_3)C_2H_5{}^+I^-$ |
| 54 | $\{(CH_3)_3SiO\}_3Si(CH_2)_3N(CH_3)_2$ |
| 55 | $O\{Si(CH_3)_2(CH_2)_3NHCH_2CH_2NH_2\}_2$ |
| 56 | $\{(CH_3)_3SiO\}_2SiCH_3(CH_2)_3NHCH_2CH_2NH_2$ |

[j]Zephiran ® is a mixture of alkyl (40% $C_{12}$, 50% $C_{14}$, 10% $C_{16}$) benzyldimethylammonium chlorides. (Winthrop Laboratories)

TABLE I

Percent Reduction Of Viable Cells Of *Escherichia coli*-B By Surfaces Treated By The "Paint-on" Technique

| Test No. | Substrate | Solvent | g. ion/ 100 Å$^2$ | % Reduction Unwashed | % Reduction Washed |
|---|---|---|---|---|---|
| 1 | ®Minusil[a] | Methanol | 10 | 100 | |
| 2 | " | " | 8.2 | 90 | 85 |
| 3 | " | " | 0.2[b] | | 94 |
| 4 | Cellulose | Water | 540 | 30 | 77 |
| | Acetate[c] | | | | |
| 5 | ®Ludox[d] | " | | 100 | 100 |
| 6 | S/AN[e] | Water | 8.2[b] | | 52 |
| 7 | " | " | .14[b] | | 38 |
| 8 | $(CH_3SiO_{3/2})_n$[f] | " | | 100 | 100 |
| 9 | $(CH_3SiO_{3/2})_n$[g] | " | (g) | 100 | 37 |
| 10 | Minusil | " | 10.5 | 62 | 51 |
| 11 | Minusil | Ethanol | 9.4 | | 100 |
| 13 | " | " | 0.03[h] | | 100[h] |
| 14 | S/AN | " | 15.1 | 100 | 100 |
| 15 | ®Cabosil[i] | Hexane | 0.1 | 70 | |
| 16 | Minusil | Methanol | 10 | 100 | 100 |
| 17 | " | Water | 10 | 100 | 24 |
| 18 | S/AN | Water | 10 | 44 | 18 |
| 19 | Minusil | Methanol | 10 | 99 | 90 |
| 20 | " | " | 10 | 100 | 100 |
| 21 | " | " | 10 | 100 | 93 |
| 22 | " | " | 10 | 53 | 38 |
| 23 | S/AN | " | 10 | 64 | 45 |
| 24 | Minusil | " | 10 | 23 | 0 |
| 25 | S/AN | " | 10 | 100 | 46 |
| 26 | Minusil | Methanol | 10 | 25 | 14 |
| 27 | S/AN | " | 10 | 24 | 17 |
| 28 | Minusil | Water | 10 | 99 | 90 |
| 29 | Cellulose Acetate | " | 10 | 95 | 100 |
| 30 | S/AN | " | 10 | 84 | 30 |
| 31 | Minusil | " | 10 | 91 | |
| 32 | " | Methanol | 10 | 87 | 43 |
| 33 | " | " | 10 | 69 | 33 |
| 34 | " | " | 10 | 100 | |
| 35 | " | Hexane | 130 | 100 | 97 |
| 36 | Cellulose Acetate | Water | 10 | 100 | 100 |
| 37 | Minusil | Hexane | 10 | 100 | 100 |
| 38 | " | Methanol | 10 | 100 | 100 |
| 39 | " | Water | 10 | 60 | 21 |
| 40 | Ludox | " | 10 | 100 | 100[k] |
| 41 | S/AN | " | 10 | 97 | 14 |
| 42 | " | " | 10 | 63 | 57 |
| 43 | Minusil | Hexane | 10 | 98 | 96 |
| 44 | " | Methanol | 10 | 100 | 100 |
| 45 | " | Ethanol | 1 | 75 | |
| 46 | S/AN | Water | 10 | 100 | 100 |
| 47 | Minusil | " | 100 | 100 | 23 |
| 48 | " | " | 100 | 100 | 20 |
| 49 | " | " | 10 | 100 | 96 |
| 50 | " | " | 10 | 100 | 91 |
| 51 | " | " | 10 | 96 | 83 |
| 52 | S/AN | " | 10 | 100 | |
| 53 | Minusil | " | 10 | 100 | 65 |
| 54 | " | Hexane | 10 | 100 | 48 |
| 55 | " | " | 164 | 100 | 100 |
| 56 | " | " | 170 | 100 | 100 |

[a]99.9+% silica, 10μ particle size, 1.1 m$^2$/g surface area (Pennsylvania Glass Sand, Co.)
[b]This sample was prepared with radioactive $(CH_3)_3{}^{14}CH_3N^+Cl$ by Substantive Method.
[c]Cellulose Acetate fiber, 10 denier 0.1 m$^2$/g surface area (Celanese Corp.)
[d]Ludox-HS, 30% silica sol in water, pH 9.8, 210 m$^2$/g surface area 15 mμ particle size.
[e]S/AN, Styrene-Acrylonitrile microcapsules, 1 to 20μ particle size, 0.63 m$^2$/g surface area (Dow Chemical Co.)
[f]Methyltrimethoxysilane (13.7 g., 0.1 mole) and tetramethylammonium chloride (1.2 g., 0.015 mole) was dissolved in 5 ml. of water and methanol and water was distilled from the solution as a polymeric gel formed. The gel was dried to an insoluble white solid which was ground to a fine powder. The powder was washed exhaustively with water until the wash water contained no detectable chloride ion by test with silver nitrate.
[g]Same as (f) with sodium chloride. Unwashed powder contained 2.6% Na$^+$, 0.79% Cl$^-$, washed powder contained 0.07% Na$^+$, nil Cl$^-$.
[h]Prepared with $C_{18}H_{37}N(CH_3)_2{}^{14}CH_3{}^+I^-$ applied at a low level and washed with water, ethanol and dilute hydrochloric acid. Concentration of the radioactive cation on the solid was measured by radioactive assay.
[i]Cabosil MS-75, silica aerogel, 12–15 mμ particle size, 274 m$^2$/g (Cabot Corp).
[k]Washed exhaustively with water until free of detectable chloride ion.

The data shown in Table I indicates a number of unexpected effects. Most surprising is the fact that every substance tested by the Powder Test displayed antimicrobial behavior. This was most surprising since many of the substances have little or no antimicrobial activity in solution.

The most widely standardized method of measuring antimicrobial activity of any substance is probably that of Serial Tube Dilution. In this technique, 1 g. of substance is mixed with 9 ml. of sterile broth in a sterile glass tube. One ml. of this mixture is transferred aseptically to a second tube containing 9 ml. of broth to create a 1/100 dilution of the substance being tested. This is repeated to form a series of dilutions each increasing by a factor of 10. Thus 1/10, 1/100, 1/1000, 1/10,000 etc. The broth is selected to contain vitamins, amino acids, sugars, etc. selected for optimum growth of the microorganism to be used for the test.

Each of the series of tubes is inoculated with about 0.1 ml. of a test organism and incubated for 24 hours at 37° C. for bacterial growth or at 25° C. for fungal growth. After incubation the most dilute concentration of substance to inhibit growth of the organism is recorded as the Minimum Inhibitory Concentration (MIC). This is usually expressed as parts per million (PPM) or $\mu$g/ml., i.e. in parts by weight of broth.

In most of the tests of Table I, the amount of the substance tested in the Powder-test was insufficient to kill the E. coli-B by dissolving from the substrates to enter the culture. Calculations of the $\mu$g of substances on the unwashed samples, if completely dissolved in 0.1 ml. of culture, indicate that such solution could not equal the MIC of the substance. The amount of substance after washing is unknown, but it was necessarily less.

Table II indicates the MIC, for E. coli-B for examples for which this value is known and lists the maximum concentration of the substances that could be reached if all the substances were dissolved from the surfaces of the substrates. The test nos. refer to Table I.

TABLE II

| Test No. | Substance | MIC $\mu$g/ml | Max. $\mu$g/ml. in test |
|---|---|---|---|
| 3 | $(CH_3)_4N^+Cl^-$ | >10,000 | <175 |
| 10 | $NH_4^+Cl^-$ | >10,000 | <250 |
| 13 | $C_{18}H_{37}N(CH_3)_3^+I^-$ | 100 | <3 |
| 19 | $n-C_4H_9N(CH_3)_3^+Cl^-$ | >10,000 | <2700 |
| 28 | $(CH_3O)_3Si(CH_2)_3N(CH_3)_3^+Cl^-$ | >10,000 | <300 |
| 38 | $(CH_3O)_3Si(CH_2)_3NC_5H_5^+Cl^-$ | >10,000 | <3200 |
| 42 | $(CH_3O)_3Si(CH_2)_3N(CH_3)_2n-C_4H_9^+Cl^-$ | >10,000 | <2000 |
| 41 | $(CH_3O)_3Si(CH_2)_3N(CH_3)_2C_8H_{17}^+Cl^-$ | >10,000 | <2600 |
| 45 | $(CH_3O)_3Si(CH_2)_3N(CH_3)_2C_{18}H_{37}^+Cl^-$ | 1,000 | <200 |

The examples of Table I indicated that every substance that dissolved in water and ionized in water to form cations other than protons were capable of making surfaces antimicrobial as measured by the Powder-Test. Every salt was effective and every amine. Amines are well known to dissolve in water to form ammonium hydroxides, e.g. $R_3N+H_2O \rightleftharpoons R_3NH^+ + OH^-$.

The fact that certain substrates that had been treated with chloride salts and were washed until free or almost free of chloride ion, indicated that the cation from each substance was the essential activating species that caused surfaces to exhibit antimicrobial behavior.

This was most surprising and also most evident with examples such as No. 9, $Na^+Cl^-$; No. 7, $(CH_3)_4N^+Cl^-$; No. 13, $C_{18}H_{37}N(CH_3)_3^+I^-$; or No. 40, $(CH_3O)_3Si(CH_2)_3NC_5H_5^+Cl^-$. The salt of No. 40 has an N/Cl ratio of unity, but elemental analysis of the washed Ludox indicated an N/Cl ratio of about 296/1. Although essentially all of the chloride ion was not on the substrate, the surface was highly anti-microbial.

EXAMPLE 2

To gain an analytical capability to show what occurred on a surface that caused it to become antimicrobial, typical substances were made radioactive. Radiotracer techniques were then applied to measure accurately very low concentrations of the substances and to locate the substances. (A) $(CH_3)_3N^{14}CH_3^+Cl^-$ was prepared by sealing $^{14}C$-methylchloride (1.96 mg., 0.039 m mole), (0.252 m Ci) with methylchloride (218.3 mg., 4.5 m mole) in methanol (0.83 g) and trimethylamine (1.8118 g., 30.71 m mole) in a flask at room temperature. Crystals formed until the mixture solidified. Vacuum was applied to remove all volatile materials leaving 2.9616 g. of fine white crystals of radioactive tetramethylammonium chloride with an activity of 0.025 mCi/g. (B) $C_{18}H_{37}N(CH_3)_2^{14}CH_3^+I^-$ was made in essentially the same way from $C_{18}H_{37}N(CH_3)_2$, $CH_3I$ and $^{14}CH_3I$ in methanol. The product was recrystallized from ethanol to obtain 520.9 mg. with an activity of 3.28 mCi/g. (C) $(CH_3O)_3Si(CH_2)_3N(CH_3)_2^{14}CH_2C_{17}H_{35}^+Cl^-$ was made from octadecyl-1-$^{14}C$ chloride in hexane with $(CH_3O)_3Si(CH_2)_3N(CH_3)_2$ in methanol in a sealed glass tube at 110° for 70 hours. The product was washed with hexane and dried to give 10 mg. of crystals with an activity of 1 mCi/m mole. The hexane was used to dissolve and recrystallize 967.7 mg. of $(CH_3O)_3Si(CH_2)_3N(CH_3)_2C_{18}H_{37}^+Cl^-$ to obtain 1.023 g. of radioactive crystals with a specific activity of 0.36 mCi/m mole. (D) $(CH_3O)_3Si(CH_2)_3N(CH_3)_2^{14}CH_3^+Cl^-$ was prepared from 3-dimethylaminopropyltrimethoxysilane (2.44 g., 12 m moles) in methanol (1.0 g) and $^{14}CH_3Cl$ (3.89 mg., 0.5 mCi) at 100° C. for 2 hrs in a sealed ampoule. All volatile materials were removed from the product under vacuum leaving white crystals (2.98 g., 98% yield).

Solutions of (B), (C), (D) were prepared in distilled water, each $10^{-3}$ M concentrations. Each of these solutions was stirred with sufficient Minusil so that if the solutions were depleted of (B), (C) or (D), the Minusil should have 10 molecules of radio-cations per 100 Å$^2$ of the surface of the Minusil. The stirring was for the time and at the temperatures indicated in Table III. The Minusil was removed from the solutions, washed repeatedly with water and assayed.

TABLE III

| | Rate and Level of Adsorption on Minusil | | |
|---|---|---|---|
| Substance | °C. | Hours | g-ion/100 Å$^2$ |
| (B) | 25 | 2 | 1 |
| | 25 | 24 | 1 |
| | 60 | 2 | 1 |
| | 60 | 24 | 1 |
| (C) | 25 | 2 | 3.8 |
| | 25 | 24 | 4.8 |
| | 25 | 168 | 7.2 |
| | 25 | 336 | 7.4 |
| | 60 | 2 | 6.5 |
| | 60 | 4 | 7.8 |
| | 60 | 24 | 9.62 |
| (D) | 25 | Seconds | .7 |
| | 25 | Seconds | .13[a] |

[a]Cellulose Acetate fibers, 0.12 m$^2$/g surface area.

These data indicate that the adsorption of (B) was limited to one molecule/100 Å$^2$, but that (C) was adsorbed without limit until the solution was depleted.

This method in which the cations are adsorbed by a surface from a very dilute solution is referred to as the Substantive Method. This method is not like that of the Paint-on Technique by which all of a substance is coated onto or mixed with surfaces. Both methods produce active surfaces, but the surfaces are not necessarily the same.

By the Paint-on Technique (D) was put onto Minusil and Cellulose Acetate fiber and the effect of water washing, level of treatment and the effect of drying the solids before they were washed was studied.

TABLE IV (D) $(CH_3O)_3Si(CH_2)_3N(CH_3)_2{}^{14}CH_3{}^+Cl^-$ on Minusil

| Temp. of Drying °C. | g-ion/100 Å$^2$ | | |
|---|---|---|---|
| | initially | 1 wash | 2 wash |
| ~25 | 2.3 | 1 | 1 |
| ~25 | 9.5 | 1.8 | 1 |
| 70 | 9.3 | 1.4 | 1 |
| 100 | 4.6 | 1.1 | |
| ~25 | 4.8 | 1.1 | |
| ~25 | 25.5 | 2.4 | 1.3 |
| ~25 | 20$^a$ | .9$^a$ | |

$^a$Cellulose Acetate

The Substantive Method was employed at room temperature by stirring powders for 2 hours with enough (C) to apply 10 molecules/100 Å$^2$. After 2 hours, the powders were separated in a centrifuge. They were assayed and then water washed 3 times in a centrifuge and assayed again.

TABLE V

Substantive Treatment With (C) At Room Temperature

| Substrate | g. ion/100 Å$^2$ of surface | |
|---|---|---|
| | As Prepared | Washed |
| Minusil | 3.8 | 3.7 |
| S/AN | 7.6 | 6.9 |
| Teflon$^a$ | 2.5 | 2.3 |

$^a$Finely powdered Teflon, 0.012 m$^2$/g surface area.

These data indicate that such diverse surfaces as silica, polystyrene-acrylonitrile, cellulose acetate and Teflon adsorb cations. The rate at which the ions are adsorbed is very fast for the first molecular layer of ions. Compounds (B) and (D) are adsorbed very strongly up to approximately a limit of one molecular layer. Compound C is adsorbed slowly after about the first molecular layer, but it is adsorbed without limit until the solution is depleted. If excess (B) and (D) is applied by the paint-on technique, excess is removable by water until the level near one molecular level remains.

Every sample in Tables III, IV and V have near 100% reduction of E. coli-B in the powder test.

Fibers of Cellulose Acetate, Polyester and Nylon-66 (0.47 to 0.49 g) were stirred in 100 ml. of 0.001% $(CH_3O)_3Si(CH_2)_3N(CH_3)_2{}^{14}CH_2C_{17}H_{35}{}^+Cl^-$ in water at room temperature. Periodically 0.1 ml. of the solution was withdrawn and assayed in a liquid scintillation spectrometer to measure the rate at which the solution was depleted of radioactive cations. After 24 hours the fibers were washed thoroughly with distilled water and assayed.

TABLE VI

Substantive Treatment of Fibers with $(CH_3O)_3Si(CH_2)_3N(CH_3)_2{}^{14}CH_2C_{17}H_{35}{}^+Cl^-$

| | Decompositions/min/g of Solution | | | | |
|---|---|---|---|---|---|
| | Cellulose Acetate | | | Polyester | Nylon-66 |
| Minutes | pH 5 | pH 7.5 | pH 10 | pH 7.5 | pH 7.5 |
| 0.0 | 159 | 163 | 167 | 169 | 167 |
| 0.5 | 121 | 125 | 114 | | |
| 5 | 118 | 116 | 102 | 126 | 102 |
| 15 | 100 | 107 | 97 | 102 | 104 |
| 30 | 94 | 99 | 93 | 81 | 94 |
| 1440 | 52 | 56 | 71 | | 89 |
| Count on Washed Samples dec/min/g | 14,581 | 16,317 | 20,808 | 18,483 | 14,719 |
| Cations/100 Å$^2$ of Surface | 1.3 | 1.4 | 1.8 | 1.6 | 0.8 |

Cellulose acetate fibers in a 1% solution as above adsorbed 210 cations/100 Å$^2$ of surface.

Fibers (10 g.) of Cellulose Acetate, Polyester, Cotton and Fiberglass were stirred in 100 ml. of 0.4% $(CH_3O)_3Si(CH_2)_3N(CH_3)_2{}^{14}CH_2C_{17}H_{35}{}^+Cl^-$ in water at room temperature. The stirring was for a short time until they were thoroughly wetted by the solution. They were then taken from the solution, pressed as dry as possible on filter paper and assayed for radioactivity.

The samples were then washed with distilled water for five hours with a change of water every 10 minutes for the first hour and every hour for four hours.

TABLE VII

| Fiber | Initial Activity mCi/g | After Washing mCi/g |
|---|---|---|
| Polyester | .49 | .15 |
| Cotton | .82 | .69 |
| Cellulose Acetate | .45 | .44 |
| Fiberglass | .50 | .16 |

The polyester fiber (0.5 g) was soaked in 0.01% concentration of above solution for 24 hrs. and assayed. The fiber had adsorbed 3 cations/100 Å$^2$ of surface.

A second (0.5 g) sample was soaked in the same solution for 24 hours. This sample adsorbed 2 cations/100 Å$^2$ of surface.

A third sample (0.5 g) was soaked in the same solution 74 hours. This sample adsorbed 5 cations/100 Å$^2$ of surface.

A fourth sample (0.5 g) was soaked in the same solution 24 hours. This sample adsorbed less than 1 cation/100 Å$^2$ of surface.

The solution was then assayed and had no detectable radioactivity, indicating that the solution had been depleted of all radio cations.

EXAMPLE 3

Minusil was treated with $C_{18}H_{37}N(CH_3)_3{}^+{}^{36}Cl^-$ as nearly identically as possible to the sample in Table III. A solution in water that contained $21.28 \times 10^{-6}$ moles of chloride at a specific activity of 77.823 dpm/μmol of Cl$^-$ was used to treat 1.0073 g. of 10μ Minusil.

Unwashed powder indicated only 0.16 Cl$^-$ per 100 Å$^2$ of surface. One wash with 15 ml. of water reduced the Cl$^-$ level to zero within the limits of detection of $^{36}$Cl$^-$, which we estimate to be about 0.005 Cl$^-$/100 Å$^2$.

The activity of the water remained unchanged during this experiment indicating all of the chloride ion remained in the water and none became adsorbed onto the Minusil although 1 cation/100 Å$^2$ of surface was adsorbed.

This is taken as compelling evidence that the cation was adsorbed onto the surface by a process of ion exchange, most likely described by an equation such as

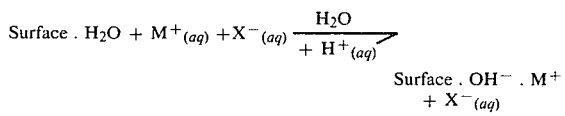

In this equation, M$^+$ is a cation other than H$^+$, and an H$^+$ is displaced from water adsorbed onto the substrate to become hydrated and to enter the aqueous phase as H$^+_{(aq)}$.

Our data indicates that this equation is quantitatively accurate up to the point that the concentration of M$^+$ near the surface of the substrate reaches a limit of about one M$^+$ ion/100 Å$^2$ of surface area.

A sample of Minusil with one non-radioactive Me$_3$NC$_{18}$H$_{37}^+$ cation per 100 Å$^2$ was stirred in a dilute aqueous solution that contained a large excess of C$_{18}$H$_{37}$N(CH$_3$)$_2^{14}$CH$_3^+$ cations. After two hours at room temperature, the Minusil assayed as having 1.0 radioactive cations/100 Å$^2$ of surface.

This indicated that the process of ion exchange took place between radioactive and non-radioactive cations on the surface and that an equilibrium was established rapidly in this example. Thus:

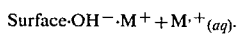

This further indicates that simple cations do not adsorb beyond one cation per 100 Å$^2$ by the Substantive Method from dilute solutions.

A sample of Minusil with one non-radioactive Me$_3$NC$_{18}$H$_{37}^+$ cation per 100 Å$^2$ was stirred with a dilute aqueous solution containing a large excess of (CH$_3$)$_3$N$^{14}$CH$_3^+$Cl$^-$ as above. Subsequent assay showed no activity on the surface.

This indicated that a small cation such as (CH$_3$)$_4$N$^+$ cannot measurably displace a large one according to the above equation.

This agrees with commonly accepted theory that cations that associate in solution, e.g., form micelles at suitable concentrations, adsorb to solids much more strongly than do smaller cations.

EXAMPLE 4

The experiments of Example 3 which used (CH$_3$O)$_3$Si(CH$_2$)$_3$N(CH$_3$)$_2^{14}$CH$_2$C$_{17}$H$_{35}^+$Cl$^-$ were repeated with (CH$_3$O)$_3$Si(CH$_2$)$_3$N(CH$_3$)$_2$C$_{18}$H$_{37}^{+36}$Cl$^-$.

Minusil in Table III which had adsorbed 3.8 cations/100 Å$^2$ was assayed for $^{36}$Cl$^-$ and 1.89 $^{36}$Cl$^-$ ions/100 Å$^2$ was found. The sample was washed further and the $^{36}$Cl$^-$ was reduced to 1.1 $^{36}$Cl$^-$ ions/100 Å$^2$.

Minusil (1 g.) was stirred at 60° C. for 24 hours with 2×10$^{-3}$ Molar solutions (100 ml) of (CH$_3$O)$_3$Si(CH$_2$)$_3$N(CH$_3$)$_2^{14}$CH$_2$C$_{17}$H$_{35}^+$Cl$^-$ and of (CH$_3$O)$_3$Si(CH$_2$)$_3$N(CH$_3$)$_2$C$_{18}$H$_{37}^{+36}$Cl$^-$. Assay of these samples showed 16.3 cations and 4.3 anions per 100 Å$^2$ of surface. Exhaustive water washing of these samples had very little effect upon these values. Washing with ethanol reduced them to 13.4 cations and 1.0 anions/100 Å$^2$.

A mixture of 92 mg (CH$_3$O)$_3$Si(CH$_2$)$_3$N(CH$_3$)$_2^{14}$CH$_2$C$_{17}$H$_{35}^+$Cl$^-$ and 2.1851 g. (CH$_3$O)$_3$Si(CH$_2$)$_3$N(CH$_3$)$_2$C$_{18}$H$_{37}^+$Cl$^-$ was hydrolyzed with water and freed of all volatiles under vacuum at room temperature or below to obtain a powder essentially (HO)$_3$Si(CH$_2$)$_3$N(CH$_3$)$_2$C$_{18}$H$_{37}^+$Cl$^-$ with a specific activity of 1.4719×10$^8$ dpm/g.

The experiment was repeated with 3.1 g. of (CH$_3$O)$_3$Si(CH$_2$)$_3$N(CH$_3$)$_2$C$_{18}$H$_{37}^{+36}$Cl$^-$.

Solutions of these salts, 7×10$^{-4}$ Molar and 0.40 g. of Minusil were stirred 2 hours at room temperature and water washed. The Minusil adsorbed 3.5 cations/100 Å$^2$, nearly duplicating the value in Table III under nearly the same conditions. The Minusil had adsorbed no detectable level of $^{36}$Cl$^-$.

These data indicate that the adsorption of the silyl substituted salt differed from the adsorption of a simple ammonium salt, by not being limited to one cation/100 Å$^2$ of surface. Adsorption beyond this level included some part which was adsorbed as an ion pair. If adsorption was from sufficiently dilute solution, or if the surface was subjected to sufficient washing, most or all of the anions were absent from the surface.

Precipitation of the polymeric hydrolyzate of (CH$_3$O)$_3$Si(CH$_2$)$_3$N(CH$_3$)$_2$C$_{18}$H$_{37}^+$Cl$^-$ from dilute solution in water in the absence of a substrate occurs slowly. The precipitate was filtered from the water, dried and analyzed for chloride ion. The level was too low to measure by non-radiotracer techniques. The dried precipitate was ground to a powder and gave 100% reduction of E. coli-B in the powder test. The precipitate when dried at 100° C. is polymeric and no longer soluble in water.

These data indicate that the silyl substituted salts can polymerize in the absence of a substrate to form an insoluble product which is formed by a process in which ion exchange was only one part. The polymer was a polysiloxane containing polymer units approximately described as HO−O$_{3/2}$Si(CH$_2$)$_3$N$^+$(CH$_3$)$_2$C$_{18}$H$_{37}$Cl$^-$.

EXAMPLE 5

A sample (10 mg., 100 cm$^2$) of Minusil having 3.8 (CH$_3$O)$_3$Si(CH$_2$)$_3$N(CH$_3$)$_2^{14}$CH$_2$C$_{17}$H$_{35}^+$ cations per 100 cm$^2$ of surface was added to 2 ml of resting state E. coli-B culture containing 3750 cells/ml in a small closed vial, Vial-1.

A sample (10 mg) of untreated Minusil was added to 2 ml of the cells in Vial-2.

Only the culture was added to Vial-3.

The three vials were fastened to a wheel at a 45° angle and tipped end for end 24 times/min. as the wheel rotated in an incubator at 37° C. Samples were removed from the vials periodically and counts were made of the viable cells/ml. at various times. The results are shown in Table VIII.

TABLE VIII

| | Viable Cells/ml E. coli-B | | |
|---|---|---|---|
| Minutes | Vial-3 | Vial-2 | Vial-1 |
| 0 | 3750 | 3750 | 3750 |
| 5 | 4370 | 3900 | 1600 |
| 15 | 5000 | 3700 | 29 |
| 30 | 4200 | 4300 | 1 |
| 45 | 4100 | | 3 |

TABLE VIII-continued

| | Viable Cells/ml E. coli-B | | |
|---|---|---|---|
| Minutes | Vial-3 | Vial-2 | Vial-1 |
| 60 | | 4400 | 0 |

Vials 3 and 2 showed an increase in the number of cells. Vial-1 contained no more than about 4 μg of active substance per ml. of culture, or less than 4% of the (MIC) for the substance. Under the conditions of this test, this small amount caused rapid reduction in the number of viable organisms in the culture.

A plot of the logarithm of the number of viable cells versus time for the cells in Vial-1 gave a straight line. See FIG. 1, which is a plot of the number of viable cells on a log$_{10}$ scale versus minutes on a linear scale.

This plot indicates that the organisms were killed by physical contact with the treated surface and that the rate of decrease in the number that were viable under standardized conditions of agitation followed a mathematical equation very like one for the equation for the kinetics of a second order reaction. Thus the rate of decrease is:

$$-\frac{dS}{dt} = K \{\text{area of surface/ml}\}\{S\}$$

in which
S = Concentration of viable organisms/ml
K = A specific rate constant
t = time During an experiment the area remains constant. Integration therefore gives:

$$-Ln\ S = K\{\text{Area/ml}\}t + \text{constant}$$

a plot of Ln S versus t called for by this equation is a straightline with a slope = K{area/ml}.

A convenient way to determine K is from the equation $$Ln\ S_t/S_o = K\{\text{area/ml}\}(t_o + t)$$

where $S_o$ is the concentration of organisms at $t_o$ and $S_t$ is the concentration of organisms at time, t.

The time required to kill half of the organisms can be $t_{1/2}$ and $$Ln\ 0.5 = 0.693 = K\{\text{area/ml}\}t_{1/2}$$

From FIG. 1, $t_{1/2}$ is about 3.25 minutes and area/ml = 50 cm$^2$/ml. Then K = 0.004 ml/cm$^2$/min.

This calculation says that the treated surface under these conditions of agitation killed half of the organisms every 3.25 minutes and it continued to do this until the viable organisms were very few. Experimentally, viable organisms vanished in about ½ hr. although mathematically this should require an infinite amount of time.

Experiments were repeated with a range of concentrations of cells, $S_o$ and surface areas/ml, see Table IX.

TABLE IX

| cm$^2$/ml | Viable Cells of E. coli-B- S$_o$ | Minusil- t$_{\frac{1}{2}}$ | K(ml/cm$^2$/min) |
|---|---|---|---|
| 25 | 10,270 | 5.16 | 0.005 |
| 50 | 4,639,000 | 3.2 | 0.004 |
| | | 3.0$^{(a)}$ | 0.005$^{(a)}$ |

TABLE IX-continued

| cm$^2$/ml | Viable Cells of E. coli-B- S$_o$ | Minusil- t$_{\frac{1}{2}}$ | K(ml/cm$^2$/min) |
|---|---|---|---|
| | | 7 | 0.002$^{(b)}$ |
| | 8,243 | 3.6 | 0.004 |
| | 3,750 | 3.3 | 0.004 |
| | 1,459 | 1.7 | 0.008 |
| | 992 | 3.3$^{(a)}$ | 0.004$^{(a)}$ |
| 100 | 7,502 | 1.75 | 0.004 |
| | 1,314 | 1.68 | 0.004 |

$^{(a)}$surface of S/AN
$^{(b)}$substance (CH$_3$O)$_3$Si(CH$_2$)$_3$N(CH$_3$)$_3^+$Cl The samples of Minusil and S/AN shown in Table V were studied to see what effect the level of treatment of a surface has upon the specific rate constant K. The results are shown in Table X.

(CH$_3$O)$_3$Si(CH$_2$)$_3$N(CH$_3$)$_2$C$_{18}$H$_{37}^+$Cl$^-$ (25 g.) was dissolved in 34.5 g. of methanol. Distilled water (15 g.) was added to the solution which was then heated to reflux and then all volatiles were removed under vacuum leaving a solid polymer, essentially {O$_3$/2Si(CH$_2$)$_3$N(CH$_3$)$_2$C$_{18}$H$_{37}^+$Cl$^-$}$_n$. This solid was ground to a fine powder and washed with water. It was essentially insoluble in water. It was washed with ethanol and isopropanol and lost less than 2% by weight during these washings. The washed powder was dried and ground again and sieved. Particles smaller than 150 μm were tested. The area/g of this powder was not accurately known, so K for this powder could only be approximated as the 10 mg. of this powder had an area equal to 10 mg. of Minusil.

TABLE X

| Substance | molecules/ 100 Å$^2$ | Substrate | K(ml/cm$^2$/min) | |
|---|---|---|---|---|
| | | | E.coli-B | P Aeruginosa |
| C$^{(a)}$ | 1 | Minusil | 0.002 | 0.003 |
| | | S/AN | 0.001 | 0.001 |
| | 7 | Minusil | 0.006 | 0.001 |
| | | S/AN | 0.004 | 0.005 |
| | not applicable | none | | 0.008 |
| B$^{(b)}$ | 1 | Minusil | 0.008 | 0.002 |
| | | S/AN | 0.003 | 0.001 |
| | 7 | Minusil | 0.004 | |
| | | S/AN | 0.002 | |

$^{(a)}$C is (CH$_3$O)$_3$Si(CH$_2$)$_3$N(CH$_3$)$_2$C$_{18}$H$_{37}^+$Cl$^-$
$^{(b)}$B is C$_{18}$H$_{37}$N(CH$_3$)$_3^+$Cl

These data in Tables IX and X indicate that the surfaces have remarkably similar effects upon organisms. Multiple layers of the organic cation may slightly reduce the activity of a surface. Data of Table III suggests that layers of the organic cation would be removed during the test until only one layer remained. Thus the activity measured in this manner for a simple cation, most probably is that of an adsorbed level one cation thick on the substrate.

Multiple layers of the silyl-substituted cation seem to slightly increase the activity of the surface. The solid polymeric substance had an activity similar to that of a substrate with numerous layers of adsorbed cations. This suggests that as the number of layers of these cations increase, the effects of the substrate vanish, so that a substrate coated with multiple layers of a substance and the polymeric substance alone present very similar effects upon contact with organisms.

EXAMPLE 6

Nylon fibers were treated with sufficient dilute solution of (CH$_3$O)$_3$Si(CH$_2$)$_3$N(CH$_3$)$_2$C$_{18}$H$_{37}^+$Cl$^-$ in water to deposit 0.1% by weight upon the fiber if the solution were depleted. The fibers were washed with water and submitted to the test described in Example 5.

This time 3 ml. of a tryptic soy broth was inoculated with 1 ml. of an 18 hour culture of *Staphylococcus aureus* FDA-209 to give 4 ml. of liquid in the vials which were rotated 29 times/minute and approximately 10 mg. of fiber was tested. The surface area per gram of this fiber was not known, but it was much less than that of the samples in Example 5.

TABLE XI

| Viable cells of *S. aureus* in Tryptic soy broth | | | |
|---|---|---|---|
| Minutes | Vial-3 | Vial-2 | Vial-1 |
| 0 | 19,000 | 19,000 | 19,000 |
| 30 | 38,000 | 20,000 | 16,000 |
| 60 | | 25,000 | 11,000 |
| 90 | 45,000 | | 7,000 |
| 120 | 100,000 | | 4,600 |
| 150 | 150,000 | 60,000 | 1,200 |
| 180 | | 90,000 | 700 |

The logarithm of the number of viable cells in Vial-1 plotted versus time was a slightly concave curve. This is due to the fact that in the nutrient medium, cells were multiplying during this test, so that the net rate of their decrease was the difference between the rates at which they were dying and at which they were multiplying.

The experiment was repeated with 3 ml. of sterile brine replacing the soy broth.

TABLE XII

| Viable cells of *S. aureus* in Sterile Brine | | |
|---|---|---|
| Minutes | Vial-2 | Vial-1 |
| 0 | 15,000 | 15,000 |
| 30 | 4,000 | 880 |
| 60 | 2,000 | 15 |
| 90 | 1,500 | 2 |
| 120 | 1,500 | 0 |

The logarithm of the number of viable cells in Vial-1 in this case plotted versus time was a straight line as in FIG. 1.

EXAMPLE 7

A $\frac{1}{4}'' \times 7''$ piece of polyethylene tubing was filled with 6" of fine sand, 6.920 g., (0.012 m$^2$/g, total area 0.083 m$^2$). A solution of 0.00538 g., sufficient for 8 molecules/100 Å$^2$ of $(CH_3O)_3Si(CH_2)_3N(CH_3)_2{}^{14}CH_2C_{18}H_{37}{}^+Cl^-$ in 10 ml. of water was permitted to drip onto the column of sand during 15 minutes, followed by 50 ml. of distilled water. The column of sand was then assayed. It was uniformly treated to a level of 0.52 to 0.56 molecules/100 Å$^2$.

The experiment was repeated with 5.218 g. of soil, which was mostly sand gently swirled in 3 ml. of the solution for $\frac{1}{2}$ hour. It then had an activity of 0.86 mCi/g.

Untreated soil (4.084 g.) was put into the polyethylene tube and treated soil (0.9757 g.) was put on top of it. Water was then trickled thru the column very slowly, 275 ml. in 120 hrs. The water was assayed and contained less than 0.8% of the radioactivity introduced as treated soil. The column of soil was assayed. All the radioactivity had remained in the top portion of treated soil. No radioactivity could be detected in the untreated portion of the soil, indicating that the active substance had not migrated during the long elution with water.

The treated soil both before and after it had been washed was tested by the Powder Test with *Staphylococcus faecalis*. In both cases a 50% reduction in viable cells was obtained over that recovered from a sample of the untreated soil.

Fine sand (2 g.) was sterilized with steam and wet with a 1% solution of $(CH_3O)_3Si(CH_2)_3N(CH_3)_2C_{18}H_{37}{}^+Cl$. Sample 1 was sucked dry on a filter. Sample 2 was heated to 70° until it was dry.

These samples were tested by the Powder Test with 500,000 cells of *Staphylococcus faecalis*, and compared with untreated sterilized sand. Recovered viable cells from Sample 1 were 5.6% and from Sample 2, 5.9% of the number recovered from untreated sand.

Diatomaceous earth (Celite-281) was treated in the same way. The Celite was divided into three samples. Sample 1 was not washed. Sample 2 was washed with 100 ml. of distilled water. Sample 3 was washed five times with 100 ml. of water. These samples were tested by the Powder Test with 500,000 cells of E. coli-B or of *S. faecalis* and retested with 2,500,000 cells of each.

Untreated Celite permitted recovery of viable cells too numerous to count. Samples 1, 2 and 3 gave no recovery of viable cells.

Sand and Celite are both silica. The superior activity of treated Celite was due to its having much more surface area per gram than the fine sand.

The Celite (0.11 g.) was stirred with 2 ml. of 1% $(CH_3O)_3Si(CH_2)_3N(CH_3)_2{}^{14}CH_2C_{18}H_{37}{}^+Cl^-$ in water and allowed to dry at room temperature. It then assayed as 69 molecules/100 Å$^2$ of the radioactive cation. It was washed with 15 ml. of distilled water 3 times and then assayed as 10 molecules/100 Å$^2$.

Celite treated with only enough substance to put 1.8, 2.5, 2.8, 2.5 molecules/100 Å$^2$ was washed as above and assayed as having 1.7, 2.3, 2.6, 2.5 molecules/100 Å$^2$.

EXAMPLE 8

The Celite from Example 7 having 2.5 cations/100 Å$^2$ (1.5% by weight) was milled into a natural rubber, heavy duty tire tread stock and cured at 300° F. for 30 minutes to prepare Sample 1.

The Celite (1.5% by weight) was also milled into a passenger car-sidewall synthetic (SBR)-rubber tire stock and cured at 300° F. for 30 minutes to prepare Sample 2.

Samples of these cured rubbers with and without the Celite were washed thoroughly with water and placed into petri dishes containing tryptic soy broth. Each dish was then sprayed with a mixture of fungal spores of A. niger, A. flavus, A. versicolor, C. globosum and P. funiculosum and incubated at 25° C. for one week. At the end of one week visual inspection of the samples showed that fungi had grown extensively upon the control samples that contained no treated Celite. Sample 1 had fungi upon about 7% of its surface. Sample 2 had fungi growing upon about 2% of its surface.

EXAMPLE 9

A very thin film of Cellulose Acetate was dipped into a 2% solution of $(CH_3O)_3Si(CH_2)_3N(CH_3)_2C_{18}H_{37}{}^+Cl^-$ and hung up to dry. $1'' \times \frac{1}{2}''$ pieces of the film were submerged in cultures of E. coli-B and S. Faecalis which each contained 1,000,000 cells/ml. They were removed and then warmed to 37° C. for 30 minutes and submerged into tubes of sterile broth and warmed to 37° C. for 18 hrs.

No viable organisms were detected in the broth after this period of incubation with the treated film. Untreated film gave rise to growth of organisms in the broth. The treated films had killed every organism they had encountered when they were submerged in the cultures.

EXAMPLE 10

Six inch squares of thin Silastic ® sheet, Medical Grade Silicone Rubber, were swirled about in 100 ml. of toluene for 1.5 hours at room temperature. The toluene contained 0.2% by weight (A) $(CH_3O)_3\text{-}Si(CH_2)_3N(CH_3)_2{}^{14}CH_2C_{17}H_{35}{}^+Cl^-$ to give Sample 1. The toluene contained 0.1% by weight (B) $(CH_3O)_3\text{-}Si(CH_2)_3N(CH_3)_2{}^{14}CH_3{}^+Cl^-$ to give Sample 2.

The samples were removed from the toluene and hung up to dry at room temperature. One half of each sample was swirled about in 100 ml. of distilled water for 2½ minutes. This was repeated 3 times with the fresh water each time. The washed half of Sample 1 became Sample 3. The washed half of Sample 2 became Sample 4. These samples were assayed for the radioactive cations. Sample 1 assayed as 0.4 mg(A)/g. of Silastic ® Rubber. Sample 3 assayed as 0.4 mg(A)/g. of Silastic ® Rubber. Sample 2 assayed as 0.5 mg(B)/g. of Silastic ® Rubber. Sample 4 assayed as 0.4 mg(B)/g. of Silastic ® Rubber.

Six inch squares of the Silastic ® Rubber sheet were swirled about in a 2% by weight solution of $(CH_3O)_3\text{-}Si(CH_2)_3N(CH_3)_2C_{18}H_{37}{}^+Cl^-$ in water for a few minutes, removed from the water and dried on sterile filter paper in sterile petri dishes. Half of each square was washed with water as described immediately above.

A piece of each of the samples were placed in 20 ml. of sterile nutrient solution or in tryptic soy broth. Each example was then sprayed with a mixture of spores of A. niger, A. flavus, A. versicolor, C. globosum, and P. funiculosum and incubated for one week at 25° C.

At the end of the week the samples were examined visually. Untreated Silastic ® Rubber was overgrown completely with fungi. Unwashed samples had no fungi growing on them. Washed samples had a few spots on them, about 5% of the surfaces, upon which fungi were seen.

With these examples fungi flourished microscopically close to the treated Silastic ® Rubber but did not grow on the surfaces.

EXAMPLE 11

A typical latex paint was prepared with 100 g. of Rhoplex ® AC35X latex paint and 135 g. of a pigment slip. Paper squares were dipped into the paint and hung up to dry. (Sample A).

Two ml. of a 50% solution of $(CH_3O)_3\text{-}Si(CH_2)_3N(CH_3)_2C_{18}H_{37}{}^+Cl^-$ in methanol was stirred into the paint and paper squares were dipped into the paint and hung up to dry (Sample B).

These paper squares were then placed on the surface of malt agar in petri dishes and inoculated with spores of Pullularia pullulans ATC-9348 and incubated one month at 28°–30° C.

At the end of this time the fungus had grown over much of the squares of Sample A. Fungus was found on 2% of the surfaces of Sample B.

EXAMPLE 12

Square pieces of Ponderosa pine wood, (1.5″×1.5″×0.25″) were soaked for five minutes in 5% by weight solutions of (A) $(CH_3O)_3\text{-}Si(CH_2)_3N(CH_3)_2C_{18}H_{37}{}^+Cl^-$ and (B) $(CH_3O)_3\text{-}Si(CH_2)_3NHCH_2CH_2NH_2$.

Untreated pieces and pieces treated with (A) and (B) were placed on sterile Sabouraud agar and sprayed with a mixture of spores of A. niger, A. flavus, A. versicolor, C. globosum, and P. funiculosum and incubated at 27° for 21 days. Untreated pine was completely overgrown with fungi in three days. Pine treated with (A) had very little fungi on it in three days and no more than ¼ of its surface had fungi after 21 days. Pine treated with (B) had about ½ of its surface with fungi in 3 days. Fungi spread on this sample very slowly and it had portions still free of fungi after 21 days.

Fungi flourished in the agar microscopically close to the treated wood. These samples showed no zone of inhibition for growth of fungi near the wood.

EXAMPLE 13

An experiment was carried out to determine if multiple washings with various liquid media would decrease the activity on a treated substrate.

A commercial cellulose sponge was washed exhaustively in tap water and boiled for 45 minutes in distilled water and dried to constant weight at 80° C. Cylinders were cut from the dry sponge with a cork borer. Each cylinder weighed about 1.05 g. and was about ¾″ in diameter and 1⅜″ long.

Cylinders were wet with aqueous solutions, about 35 ml. that contained 10 mg. of $O_3/\text{-}2Si(CH_2)_3N(CH_3)_3C_{18}H_{37}{}^+Cl^-$ salt. The solution was squeezed and worked into a cylinder which swelled, softened and absorbed most of the liquid and was then labeled cylinders A. All cylinders were sterilized prior to washing in order to overcome any affect from bacteria in the sponge.

A cylinders were heated to 80° for 0.5 hr. and were labeled cylinders A′.

A and A′ cylinders were forced into a glass tube and about 345 liters of tap water/g. of dry sponge was forced thru them during 4 days.

These cylinders were labeled respectively B and B′.

An A cylinder was forced into a glass tube and one liter of homogenized milk was forced through it slowly. This was labeled Cylinder C;

An A cylinder was forced into a glass tube and one liter of Gallo brand Hardy Burgundy was forced through it slowly. This cylinder was labeled Cylinder D;

An A cylinder was forced into a glass tube and one liter of Budweiser ® Beer was forced through it slowly and this cylinder was labeled Cylinder E;

An A cylinder was forced into a glass tube and one liter of sea water was forced through it slowly and this cylinder was labeled Cylinder F.

An untreated cylinder and cylinders A, A′, B and B′ were inoculated with P. aeruginosa ATCC 870, eluted with four 10 ml. portions of sterile water, pour plated in letheen growth agar, incubated at 37° and the viable cells in the agar were counted and shown in Table XIII as number per ml.

Sponge cylinders A, B, C, D, and E were sterilized at 15 psig, 120° for 15 minutes in steam. An untreated sponge cylinder and A, B, C, D, E and F were inoculated heavily and tested as above.

TABLE XIII

| P. aeruginosa Recovered from 1 g. of Sponge | | |
|---|---|---|
| | No. of viable cells/ml. of culture | |
| | Sponge Not Sterilized | Sponge Sterilized |
| Control | 232,700 | 2,075,000 |
| A | 380 | 186,750 |
| A' | 200 | |
| B | 122,000 | 954,000 |
| B' | 184,000 | |
| C | | 934,000 |
| D | | 352,000 |
| E | | 581,000 |
| F | | 62,250 |

These data indicate that the cellulose sponge became remarkably antimicrobial treated at a very low level. Heating the sponge had very little effect upon its activity. The activity was reduced but remained high after washing exhaustively with diverse liquids.

EXAMPLE 14

Pieces of cloth were treated by the Paint-on technique with $(CH_3O)_3Si(CH_2)_3N(CH_3)_2C_{18}H_{37}{}^+Cl^-$ in water to treat the cloth to a level of 1% by weight. Some pieces were sterilized after treatment in an autoclave with steam for fifteen minutes.

A piece of Nylon cloth was treated with $(CH_3O)_3Si(CH_2)_3N(CH_3)_3{}^+Cl^-$ to give a level of 0.1% by weight.

The pieces of cloth were tested by AATCC-Test Method 100-1970, for evaluation of Antimicrobial Finishes on Fabrics with a contact time of 30 minutes.

TABLE XIV

| Type of Fabric | Type of Organism | % Reduction | |
|---|---|---|---|
| | | Initial | Sterilized |
| Cotton | S. aureus | 93 | 92 |
| | K. pneumoniae | 81.5 | |
| Polyester | S. aureus | | 99.1 |
| | K. pneumoniae | | 68.6 |
| Nylon | S. aureus | 100 | |

The MIC of $(CH_3O)_3Si(CH_2)_3N(CH_3)_3{}^+Cl$ is very high. The compound showed no biocidal activity in solution at concentrations as high as 10% by weight against the organisms in Table XIV.

EXAMPLE 15

A colloidal dispersion of solid methylsilsesquioxane $(CH_3SiO_{3/2})_n$ particles, 10% by weight, was prepared by hydrolyzing an emulsion of methyltrimethoxysilane (10 g.) in water (37.1 g.) with 0.75 g. of $(CH_3O)_3Si(CH_2)_3N(CH_3)_2C_{18}H_{37}{}^+Cl^-$ as an emulsifier and 0.25 ml. of 1 N $NH_4OH$ as a catalyst for hydrolysis.

A second dispersion was made with (0.75 g.) $C_{12}H_{25}N(CH_3)_3{}^+Cl^-$ as the emulsifier.

Methanol liberated by hydrolysis of the methoxysilanes was removed from a portion of each dispersion by distillation at 90°–95° without disturbing the stability of the colloidal dispersions.

During these preparations the pH of the aqueous phase decreased slowly from pH 11 due to the $NH_4OH$, to a pH of 6.5 for the first example and pH 8 in the second. This change in pH indicated the ion-exchange described in Example 3 had occurred between the cationic emulsifying agents and the surfaces of the colloidal particles.

These were exceedingly small particle size dispersions with the appearance of a slightly hazy, slightly blue liquid.

The standard serial tube dilution test was used with these colloidal dispersions. No agitation was required to keep these surfaces dispersed and Brownian motion was sufficient to cause contact with organisms.

Sample 2 was active at 100 μg/ml. 100 μg. of dispersion could contain no more than 2 μg. of $C_{12}H_{25}N(CH_3)_3{}^+Cl^-$, so that the apparent MIC for this substance was decreased 100 to 1000 fold by adsorption on colloidal particles.

EXAMPLE 16

A colloidal dispersion of methylsilsesquioxane $(CH_3SiO_{3/2})_n$ particles 5% by weight was prepared in water with 0.7% dodecylbenzyldimethylammonium chloride as the dispersing agent. The colloidal particles were about 125 Å in diameter.

The serial tube dilution test indicated that the M.I.C. of this colloidal dispersion was 100 ppm for E. coli and 1000 ppm for S. aureus. This would correspond to concentrations of the cationic dispersing agent of 0.7 ppm for E. coli and 7 ppm for S. aureus.

The MIC of the dispersing agent in solution is 750 ppm for both E. coli and S. aureus. This experiment indicated that particles so small that they move by Brownian motion as colloidal particles in water contact and kill microorganisms. The activity of the cation in this example was increased by absorption on the particle by 1000 fold for E. coli and 100 fold for S. aureus.

Compare, for example, page 54, Table 22 of Dekker, supra page 3.

EXAMPLE 17

Cotton thread was treated with a 0.5% solution of $(CH_3O)_3Si(CH_2)_3N(CH_3)_2C_{18}H_{37}{}^+Cl^-$ in water and air dried. The treated thread and untreated thread were buried in soil inoculated with A. niger ATCC-9642; A. flavus, ATCC 9643; A. versicolor ATCC 11730; P. funiculosum, ATCC 9644; C. globosum ATCC 6205 as in Mil. Std. 810B. The tensile strength of the thread was measured as in ASTM D 1682.

| | Pounds/sq.in. Initial | Tensile Strength After 7 days |
|---|---|---|
| no treatment | 5.1 | 0.7 |
| treated cotton | 5.8 | 5.6 |

The treatment very effectively reduced or prevented fungal attack upon cotton.

EXAMPLE 18

Nylon cloth was treated with a 0.1% solution of $(CH_3O)_3Si(CH_2)_3N(CH_3)_2C_{18}H_{37}{}^+Cl^-$ in water and air dried. The Nylon was then sprayed with a culture of Candida albicans ATCC 10231, and the number of viable organisms recoverable from the cloth was determined.

| | Organisms recovered/ml | | |
|---|---|---|---|
| | three runs | Average | % Reduction |
| no treatment | 200/210/205 | 205 | 0 |
| treated Nylon | 22/24/18 | 21 | 90 |

Cotton cloth was treated in the same way and tested with Trichophyton interdigitale ATCC 9533.

| | % surface growth in 28 days | |
|---|---|---|
| | | Average % |
| no treatment | 100/100/100 | 100 |
| treated cotton | 20/20/10 | 17 |

A polyester-cotton cloth was treated with a 0.33% solution in the same way and sprayed with cultures of the following organisms and the numbers recoverable were measured.

| | No. of Organisms/ml after 6 hrs. | | |
|---|---|---|---|
| Organism | Untreated | Treated | % Reduction |
| Micrococcus sp. | 215,500 | 2,700 | 99 |
| Staph. epidermidis | 58,000 | 3,000 | 95 |
| Enterobacter-aglomerans | 1,355,000 | 16,500 | 90 |
| Acinetobacter-calcoaceticus | 3,500 | 1,000 | 72 |
| Micrococcus sp. | 305,000 | 0 | 100 |
| | 395,000 | 200 | 99 |
| Staph. aureus | 200,000 | 200 | 99 |

EXAMPLE 19

Aerosil-200 silica manufactured by the Degussa Co., West Germany was treated in aqueous solution by mixing $(CH_3O)_3Si(CH_2)_3SC(NH_2)^+_2Cl^-$ into the water and adding the Aerosil-200 to the mixture. It was homogenized for 5 minutes using a blender. The material was then dried at 90° C. in an oven for 10–15 minutes. The silica was then formulated into a cold cream in the following manner. Two parts were prepared.

| Part A- | 2.5 gms Stearyl Alcohol | |
|---|---|---|
| | 4.0 gms White petrolatum | |
| | 0.5 gms Sorbitan Monooleate | |
| | 2.5 gms Isopropyl Myristate | |
| Part B- | Propylene glycol | 3.5 gms |
| | *Polyoxyl-40 Stearate | 1.25 gms |
| | Water | 35.8 gms |
| | Preservative Powder Prepared Above | 5% powder based on total weight of B with 1% active perservative thereon |

*Polyoxyl-40 Stearate is a polyethylene oxide stearate ester having 40 CH₂CH₂O units per stearic acid residue.

The parts A and B were heated separately to 75° C. and then B was added to A with agitation until the material became creamy and smooth. The material was slowly cooled with stirring until it began to set up and then it was allowed to cool to room temperature without stirring.

The cold cream was evaluated by a method set forth in CTFA Cosmetic Journal, Vol. 5, No. 1, "Evaluation of Methods for Determining Preservative Efficacy". Briefly, aliquots of the cream were challenged with the organisms and any growth was observed at day intervals during which time the challenged plates were incubated at 37° C. The results of this test can be found on Table XV.

TABLE XV

"Evaluation of Treated Silica in Cold Cream Formulation"
CFTA Challenge Test - Challenge Organism-
Pseudomonas Aeroginosa ATCC 15442

| | Bacterial Count | | | | | |
|---|---|---|---|---|---|---|
| Sample | Day 0 | Day 1 | Day 7 | Day 14 | Day 21 | Day 28 |
| control (no treated powder) | 7,250,000 | 10,200,000 | 615,000 | 450,000 | 500,000 | 1,825,000 |
| 5.0% powder with 1.0% active compound | 91,500 | <10 | <10 | <10 | <10 | <10 |

That which is claimed is:

1. A method of reducing the number of viable bacteria, fungi, algae and yeast in media by physically contacting the bacteria, fungi, algae and yeast with a surface which has been altered in a manner which comprises contacting a substrate, which develops a negative charge in water, with an amount effective to inhibit the growth of said microorganisms of a substance that ionizes in water to form cations and anions which substance is selected from the group consisting of sulfonium salts of the formula $R^8R^9R^{10}S^+X^-$, sulfonium salts of the formula $$O\{SiC_dH_{2d}S^+X^-\}_2$$
$$| \quad \quad |$$
$$(CH_3)_2 \ (R^{11})_2$$

isothiuronium salts of the formula $RSC(NH_2)_2^+X^-$, isothiuronium salts of the formula $$O\{SiC_dH_{2d}S^+C(NH_2)_2X^-\}_2$$
$$|$$
$$(CH_3)_2$$

phosphonium salts of the formula $R^4R^5R^6R^7P^+X^-$, and phosphonium salts of the formula $$O\{SiC_dH_{2d}P^+X^-\}_2$$
$$| \quad \quad |$$
$$(CH_3)_2 \ (R^{12})_3$$

wherein $R^8$, $R^9$ and $R^{10}$ are independently alkyl groups or aralkyl groups wherein there is a total of less than 30 carbon atoms in the molecule or a silylsubstituted alkyl radical of the formula $$Y_aSiC_nH_{2n}-$$
$$|$$
$$Q_b$$

where Y is a hydrolyzable group, Q is an alkyl radical of 1 or 2 carbon atoms or $(CH_3)_3SiO$, a has an average value of 0–3, b has an average value of 0–3, n is an integer of 1 or greater and $X^-$ is a water soluble monovalent anion, R is independently alkyl or aralkyl groups wherein there is a total of less than 20 carbon atoms in the molecule or a silylsubstituted alkyl radical of the formula

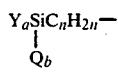

as defined above, $R^4$, $R^5$, $R^6$ and $R^7$ are as defined above for $R^8$, $R^9$ and $R^{10}$; $R^{11}$ and $R^{12}$ are independently alkyl groups or aralkyl groups wherein there is a total of less than 60 carbon atoms in the molecule and d is an integer of 1 or greater.

2. The method of claim 1 in which the microorganisms are gram-positive or gram-negative bacteria.

3. The method of claim 1 in which the microorganisms are fungi.

4. The method of claim 1 in which the microorganisms are yeasts.

5. A method as claimed in claim 1 wherein the sulfonium salt is a sulfonium halide.

6. A method as claimed in claim 5 wherein the halide is chloride.

7. A method as claimed in claim 5 wherein the halide is iodide.

8. A method as claimed in claim 5 wherein the halide is bromide.

9. A method as claimed in claim 1 wherein in the groups $R^8$, $R^9$ and $R^{10}$, at least one such group has at least 10 carbon atoms.

10. A method as claimed in claim 5 wherein the sulfonium salt is $(CH_3O)_3Si(CH_2)_3S^+(CH_3)C_{18}H_{37}I^-$.

11. A method as claimed in claim 5 wherein the sulfonium salt is $(CH_3O)_3Si(CH_2)_3S^+(CH_3)C_2H_5I^-$.

12. A method as claimed in claim 1 wherein the isothiuronium salt is an isothiuronium halide.

13. A method as claimed in claim 12 wherein the isothiuronium salt is an isothiuronium chloride.

14. A method as claimed in claim 12 wherein the isothiuronium salt is an isothiuronium iodide.

15. A method as claimed in claim 12 wherein the isothiuronium salt is an isothiuronium bromide.

16. A method as claimed in claim 12 wherein the isothiuronium salt is $(CH_3O)_3Si(CH_2)_3S^+C(NH_2)_2Cl^-$.

17. A method as claimed in claim 1 wherein the phosphonium salt is a phosphonium halide.

18. A method as claimed in claim 17 wherein the phosphonium salt is a phosphonium chloride.

19. A method as claimed in claim 17 wherein the phosphonium salt is phosphonium iodide.

20. A method as claimed in claim 17 wherein the phosphonium salt is a phosphonium bromide.

21. A method as claimed in claim 17 wherein the phosphonium salt is $(CH_3O)_3Si(CH_2)_3P^+(n-C_4H_9)_3I^-$.

22. A method as claimed in claim 21 wherein the phosphonium salt is $(CH_3O)_3Si(CH_2)_3P^+(C_6H_5)_3I^-$.

23. A method as claimed in claim 1 wherein the sulfonium salt is a sulfonium carboxylate.

24. A method as claimed in claim 1 wherein the isothiuronium salt is an isothiuronium carboxylate.

25. A method as claimed in claim 1 wherein the phosphonium salt is a phosphonium carboxylate.

26. A method of reducing the number of viable bacterial, fungi, algae and yeast in media by physically contacting the bacteria, fungi, algae and yeast with a surface which has been altered in a manner which comprises contacting a substrate, which develops a negative charge in water, with an amount effective to inhibit the growth of said microorganism of a substance that ionizes in water to form cations and anions which substance consists of an organic amine of the formula

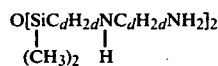

in which d in each case is an integer of 1 or greater.

* * * * *

UNITED STATES PATENT AND TRADEMARK OFFICE
CERTIFICATE OF CORRECTION

PATENT NO. : 4,259,103  
DATED : March 31, 1981  
INVENTOR(S) : James R. Malek and John L. Speier It is certified that error appears in the above-identified patent and that said Letters Patent are hereby corrected as shown below:

In Column 6, line 37; the formula reading "$H_3O$ $OH^-$" should read "$H^+$ $OH^-$".

In Column 9, line 64; the heading reading "g. ion/100 A$^2$" should read "g. ion/100 Å$^2$".

In Column 10, line 6; the heading reading "g. ion/100 A$^2$" should read "g. ion/100 Å$^2$".

In Column 12, line 55; the heading reading "g-ion/100 A$^2$" should read "g-ion/100 Å$^2$".

In Column 13, line 18; the heading reading "g-ion/100 A$^2$" should read "g-ion/100 Å$^2$".

In Column 13, line 38; the heading reading "g. ion/100 A$^2$ of surface" should read "g. ion/100 Å$^2$ of surface".

UNITED STATES PATENT AND TRADEMARK OFFICE
CERTIFICATE OF CORRECTION

PATENT NO. : 4,259,103
DATED : March 31, 1981
INVENTOR(S) : James R. Malek and John L. Speier It is certified that error appears in the above-identified patent and that said Letters Patent are hereby corrected as shown below:

In Column 12, line 43; the line reading "Solutions of (B), (C), (D) were prepared in distilled" should read "Solutions of (B), (C), and (D) were prepared in distilled".

In Column 14, line 17; the words reading "$A^2$ of" should read "$\overset{\circ}{A}{}^2$ of".

In Column 18, line 36; the heading reading "molecules/ $100\ A^2$" should read "molecules/ $100\ \overset{\circ}{A}{}^2$".

In Column 24, line 30; the word reading "absorption" should read "adsorption".

Signed and Sealed this

Sixth Day of October 1981

[SEAL]

Attest:

GERALD J. MOSSINGHOFF

Attesting Officer

Commissioner of Patents and Trademarks